United States Patent
Guthrie et al.

(10) Patent No.: US 11,318,440 B2
(45) Date of Patent: May 3, 2022

(54) CONTINUOUS FLOW REACTOR

(71) Applicant: VAPOURTEC LIMITED, Suffolk (GB)

(72) Inventors: Duncan Guthrie, Suffolk (GB); Nikzad Nikbin, Cambridge (GB); Adrian Clarkson, Suffolk (GB)

(73) Assignee: VAPOURTEC LIMITED, Bury St Edmunds (GB)

( * ) Notice: Subject to any disclaimer, the term of this patent is extended or adjusted under 35 U.S.C. 154(b) by 276 days.

(21) Appl. No.: 16/608,806

(22) PCT Filed: Apr. 23, 2018

(86) PCT No.: PCT/EP2018/060354
§ 371 (c)(1),
(2) Date: Oct. 25, 2019

(87) PCT Pub. No.: WO2018/197421
PCT Pub. Date: Nov. 1, 2018

(65) Prior Publication Data
US 2020/0206714 A1    Jul. 2, 2020

(30) Foreign Application Priority Data
Apr. 25, 2017 (GB) .................... 1706577

(51) Int. Cl.
*B01J 8/00* (2006.01)
*B01J 19/00* (2006.01)
(Continued)

(52) U.S. Cl.
CPC ........... *B01J 19/18* (2013.01); *B01J 19/0006* (2013.01); *C07K 1/045* (2013.01); *B01J 2219/00033* (2013.01); *B01J 2219/00162* (2013.01)

(58) Field of Classification Search
CPC ........ B01J 8/00; B01J 19/00; B01J 19/0006; B01J 19/0046; B01J 19/18; B01J 2208/00;
(Continued)

(56) References Cited

U.S. PATENT DOCUMENTS 3,622,553 A * 11/1971 Cines .................. C08F 2/34
526/65
4,299,794 A   11/1981 Kelley et al.
(Continued)

FOREIGN PATENT DOCUMENTS

CN    201579035 U  *  9/2010
CN    201579035 U     9/2010
(Continued)

OTHER PUBLICATIONS

UK Intellectual Property Office, Patents Act 1977: Search Report under Section 17; dated Jul. 24, 2018, Application No. GB1806565.6; pp. 2.
(Continued)

*Primary Examiner* — Natasha E Young
(74) *Attorney, Agent, or Firm* — Hackler Daghighian Martino & Novak

(57) ABSTRACT

A continuous flow reactor, a method of performing a continuous flow reaction, and a method of controlling a moveable wall of a reaction chamber of a continuous flow reactor. The reactor comprising: an inlet; an outlet; and a reaction chamber, between the inlet and the outlet and providing a flow path therebetween, the reaction chamber having a moveable wall; the reactor further comprising: a pressure sensor configured to monitor a fluid pressure in the continuous flow reactor; and a controller, operable to adjust the position of the moveable wall, and thereby change a volume of the reaction chamber, based on the monitored fluid pressure.

20 Claims, 8 Drawing Sheets

(51) Int. Cl.
*B01J 19/24* (2006.01)
*C07K 1/04* (2006.01)
*B01J 19/18* (2006.01)

(58) Field of Classification Search
CPC .... B01J 2208/00008; B01J 2208/00017; B01J 2208/00026; B01J 2208/00035; B01J 2208/0007; B01J 2208/00079; B01J 2208/00539; B01J 2208/0061; B01J 2219/00; B01J 2219/00002; B01J 2219/00027; B01J 2219/00033; B01J 2219/00049; B01J 2219/00051; B01J 2219/00054; B01J 2219/00056; B01J 2219/00065; B01J 2219/00162; B01J 2219/00182; B01J 2219/00192; B01J 2219/00222; B01J 2219/00277; B01J 2219/00274; B01J 2219/00279; B01J 2219/00281; B01J 2219/00286; B01J 2219/00288; B01J 2219/0029; B01J 2219/00351; B01J 2219/00423; B01J 2219/00583; B01J 2219/00596; B01J 2219/0068; B01J 2219/00698; B01J 2219/00718; B01J 2219/0072; B01J 2219/00725; B01J 2219/00761; C07K 1/00; C07K 1/04; C07K 1/045; G21C 1/00; C40B 50/00; C40B 50/14; C40B 60/00; C40B 60/14
See application file for complete search history.

(56) References Cited

U.S. PATENT DOCUMENTS

| | | | | |
|---|---|---|---|---|
| 5,190,075 A | * | 3/1993 | Tentler | G05D 7/0106 |
| | | | | 137/467.5 |
| 2012/0107181 A1 | | 5/2012 | Cedillo et al. | |

FOREIGN PATENT DOCUMENTS

| | | | |
|---|---|---|---|
| CN | 205216837 U | * | 5/2016 |
| CN | 205216837 U | | 5/2016 |
| EP | 0 386 238 A1 | | 9/1990 |
| EP | 0386238 A1 | * | 9/1990 ......... B01J 19/0046 |
| WO | 2004/064999 A2 | | 8/2004 |
| WO | 2010/141361 A1 | | 12/2010 |

OTHER PUBLICATIONS

International Searching Authority, Written Opinion Of The Searching Authority (PCT Rule 43bis.1) and International Search Report; International Application No. PCT/EP2018/060354, International Filing Date: Apr. 23, 2018.

Krchnak V. et al: "Color-Monitored Solid-Phase Multiple Peptide Synthesis Under Low-Pressure Continuous-Flow Conditions", Peptide Research, Natick, MA, US, vol. 3, No. 4, Jul. 1, 1990, Complete, XP000955525, ISSN: 1040-5704 11; Results and Discussion: Continuous-Flow Solid-Phase Multiple Peptide Synthesis; p. 4-5; figure 2.

Baru MB et al: "A New Feedback Control Principle in Continuous Flow Solid Phase Synthesis: Direct Monitoring of Peptide-Resin Swelling Behaviour", Peptides. Platja D'Oro, SP., Sep. 2-8, 1990; [Proceedings of the European Peptide Symposium], Leiden, Escom, NL, vol. SYM. 21, Aug. 2, 1990, pp. 198-199, XP000353585.

* cited by examiner

CONTINUOUS FLOW REACTOR

This application is a national stage application claiming priority to PCT/EP2018/060354, now WO2018/197421, filed on Apr. 23, 2018, which claims priority to Great Britain Patent Application Serial No. GB 1706577.1, filed on Apr. 25, 2017.

FIELD OF THE INVENTION

The present invention relates to a continuous flow reactor, a method of using a continuous flow reactor, and a method of controlling a moveable wall in a reaction chamber of a continuous flow reactor.

BACKGROUND

Solid phase peptide synthesis allows peptide chains to be built on a solid support by the basic steps of: attaching an amino acid to the support, deprotecting the amino acid, and coupling one or more subsequent amino acids to the attached amino acid.

Solid phase peptide synthesis can be performed in a batch reactor i.e. a fluidly static vessel where there is no flow from or to the reactor during reactions. These reactors can produce consistent results in a short period of time, but may lack a sufficiently high yield. High yields are particularly desirable in solid phase peptide synthesis, as the reaction will be repeated numerous times and therefore any losses are magnified. For example if each coupling step had a yield of 95%, after 25 repetitions of coupling the peptide would be synthesised with only a 25% yield.

Automated continuous flow reactions, particularly in the field of solid phase peptide synthesis, generally require fluids to be washed over a solid support so that reactions can be performed. These reactors may provide higher yields than batch reactors.

A problem associated with known continuous flow reactions is how to deal with the change in mass and therefore volume of reactants in the reactor. For example, in U.S. Pat. No. 9,169,287 B1, a continuous flow reactor is proposed where the reactor is not a true packed bed reactor as it contains voids and so must use large excesses of reagents, wash solvents, and reactants to ensure a complete reaction. However this process can be incredibly wasteful, and is not suitable to be scaled up to the levels that can be required for the production of biological drugs or other mass-produced peptides.

Alternatively, as is disclosed in Rodionov et al., "*A Swellographic Approach to Monitoring Continuous-Flow Solid-Phase Peptide Synthesis*", Peptide Research 1992 Vol. 5, No. 2, a pre-loaded end of the reactor may slide relative to the other, allowing an increase in volume during synthesis. However the pressure generated across the solid support is not independent of the overall fluid pressure, and this can be detrimental to reaction yields. The addition of friction of the sealing means will reduce the accuracy of the data obtained from such a reactor.

There is therefore a need for a continuous flow reactor which overcomes the above mentioned problems.

SUMMARY

At its broadest, the invention provides a continuous flow reactor where a volume of a reaction chamber is controllably adjustable in response to a reaction parameter.

Accordingly, in a first aspect, the invention provides a continuous flow reactor comprising: an inlet; an outlet; and a reaction chamber, between the inlet and the outlet and providing a flow path therebetween, the reaction chamber having a moveable wall; the reactor further comprising: a pressure sensor, configured to monitor a fluid pressure in the continuous flow reactor; and a controller, operable to adjust the position of the moveable wall, and thereby change a volume of the reaction chamber, based on the monitored fluid pressure.

Advantageously, the pressure and/or volume of the reaction chamber during a continuous flow reaction can be controllably adjusted.

Preferably the pressure sensor is arranged to measure a differential pressure between the inlet and the outlet. This allows a differential pressure across the reactor to be measured. This can allow for control of the reactor volume and/or for information about the progress of the reaction to be obtained (for example in conjunction with the reactants flowing at known and/or consistent flowrates through the reactor).

In certain configurations, the pressure sensor may comprise a first pressure sensor arranged to monitor the pressure at the inlet and a second pressure sensor arranged to monitor to the pressure at the outlet.

In further configurations, the pressure sensor may comprise a first pressure sensor arranged to monitor the pressure at the inlet, whilst the outlet is exposed to atmospheric pressure. In such an arrangement as the outlet pressure is known and therefore the differential pressure between the inlet and outlet can be determined.

In further configurations, the pressure sensor may comprise a differential pressure sensor connected between the inlet and the outlet.

The moveable wall may be connected to a drive system including a motor and a lead screw. In some embodiments, the motor may be a hybrid stepper motor, or a brushless DC motor with encoder feedback. Conveniently, this can provide a fine degree of control over the moveable wall. The drive mechanism may include a stop, configured to provide a minimum volume of the reaction chamber and/or a maximum volume of the reaction chamber. The stop in some examples can be provided by an anti-rotation bar which engages and locks an element of the drive system when the minimum or maximum volume is attained.

Alternatively, the stop may be a software stop which prohibits use of the drive mechanism to adjust the volume beyond defined limits. The stop may be a combination of one or more endstop sensor(s) and associated software trigger(s).

Conveniently, this can provide a safety device such that the pressure and/or volume of the reaction chamber does not deviate from an acceptable range.

The controller may be configured to adjust the position of the moveable wall so as to maintain the monitored pressure at a set-point in a range of 0.1 bar and 15 bar, preferably in a range of 0.5 bar to 15 bar.

The moveable wall may include a frit, which at least partially defines a wall of the reaction chamber. The frit may function to filter solid particulates from a fluid flow passing through the frit.

Advantageously, this can ensure that any solid matter useful in a continuous flow reaction (for example the solid support used in peptide synthesis) is not removed from the reaction chamber. The moveable wall may contain a fluid pathway disposed therein, fluidly connecting the reaction chamber to the outlet.

The reaction chamber may include a solid support for use in a flow reaction. The solid support may be suitable for peptide synthesis. For example, the solid support may be a Chlorotrityl Chloride resin (CTC). Other reactions can also be performed in the continuous flow reactor, particularly those which require a fixed bed where a significant change in the volume of the reactor contents can be expected as the reaction progresses. For example: oligonucleotide synthesis, carbohydrate synthesis, catalytic reactions where the catalyst is supported on a low-crosslinked polystyrene structure that is liable to volume changes.

The pressure sensor may comprise a first gauge pressure sensor to monitor a gauge pressure at the inlet and a second gauge pressure sensor to monitor a gauge pressure at the outlet. Alternatively, or additionally, the pressure sensor may monitor a differential pressure between the inlet and the outlet.

The controller may be programmable with a range (also referred to as a dead-band) of pressure changes relative to the set-point over which it will not adjust the position of the sidewall. The range may be ±0.05 bar to ±0.5 bar, preferably ±0.2 bar to ±0.5 bar. For example, the change of pressure from the set-point may need to be greater than 0.5 bar (either increasing or decreasing) or the change of pressure from the set point may need to be greater than 0.05 bar (either increasing or decreasing) before the volume of the reaction chamber will be adjusted. The range need not be symmetrical about the set-point. The range could be provided by a programmed range over which no movement of the sidewall is allowed, alternatively the gain of a signal controlling the drive mechanism may be reduced such that there is a reduced or no response of the drive mechanism.

Advantageously, this can ensure that the volume of the reaction chamber is not continuously adjusted. Continuous adjustment may be disruptive to a continuous flow reaction. For example, during peptide synthesis it has been found that continuous adjustment may cause a proportion of the peptide fragments to cleave from the resin. These cleaved fragments may be washed away and would be seen as a loss of yield.

The controller may be programmed with an asymmetric sensitivity to the monitored fluid pressure, such that it adjusts the position of the sidewall faster in response to a change in the monitored fluid pressure in one direction to another. The controller may be programmed to adjust the position of the sidewall faster when the monitored fluid pressure increases than when the monitored fluid pressure decreases.

Conveniently, this allows the reactor to respond quickly to a fast increase in monitored pressure, these being more problematic to the functioning of continuous flow reactions than fast decreases in monitored pressure.

The controller may be programmable with a value for a maximum volume of the reaction chamber; and is operable to modify the value for the maximum volume of the reaction chamber based on a stage of a continuous flow reaction. The controller may be operable to increase the value for the maximum volume of the reaction chamber during a coupling stage of a peptide synthesis reaction.

In a second aspect, the invention provides a method of performing a continuous flow reaction, comprising: supplying a fluid, via an inlet, into a reaction chamber; extracting the fluid from the reaction chamber, via an outlet; monitoring a pressure of the fluid within the continuous flow reactor; and adjusting a volume of the reaction chamber, based on the monitored fluid pressure between the inlet and the outlet.

Advantageously, the pressure and/or volume of the reaction chamber during a continuous flow reaction can be controllably adjusted.

The step of monitoring the pressure may include monitoring a differential pressure between the inlet and the outlet or vice-versa. In this way a differential pressure across the reactor can be measured. This can allow for control of the reactor volume and/or for information about the progress of the reaction to be obtained (for example in conjunction with the reactants flowing at known and/or consistent flowrates through the reactor).

In certain arrangements, the step of monitoring the pressure may include monitoring the pressure at the inlet and monitoring the pressure at the outlet.

In further arrangements, the step of monitoring the pressure may include monitoring the pressure at the inlet, whilst the outlet is exposed to atmospheric pressure. In such an arrangement, the outlet pressure is known and therefore the differential pressure between the inlet and outlet can be determined.

In further arrangements, the step of monitoring the pressure may include directly monitoring a differential pressure between the inlet and the outlet.

Adjusting the volume of the reaction chamber may be performed so as to maintain the monitored pressure at a set-point within a range of 0.1 bar to 15 bar, preferably in a range 0.5 bar to 15 bar.

The method of the second aspect may include a step of: defining a set-point for the monitored pressure and a range of pressure changes relative to the set-point over which the volume of the reaction chamber will not be adjusted. The range may be ±0.05 bar to ±0.5 bar, preferably ±0.2 bar to ±0.5 bar. For example, the change of pressure from the set-point may need to be greater than 0.5 bar (either increasing or decreasing) or the change of pressure from the set point may need to be greater than 0.05 bar (either increasing or decreasing) before the volume of the reaction chamber will be adjusted. The range need not be symmetrical about the set-point. The range could be provided by a programed range over which no movement of the sidewall is allowed, alternatively the gain of a signal controlling the drive mechanism may be reduced such that there is a reduced or no response of the drive mechanism.

The volume of the reaction chamber may be adjusted with an asymmetric speed, such that when the monitored fluid pressure changes in one direction the volume is changed at a different rate to when the monitored fluid pressure changes in another direction. The volume of the reaction chamber may be adjusted faster when the monitored fluid pressure increases than when the monitored fluid pressure decreases.

The method according to the second aspect may include the steps of: (a) supplying an amino acid containing fluid into the reaction chamber, the reaction chamber containing a solid support such that the amino acid attaches to the solid support; (b) supplying a reagent into the reaction chamber, the reagent acting to deprotect the amino acid; and (c) supplying a further amino acid containing fluid into the reaction chamber, the further amino acid coupling with the amino acid attached to the solid support. The method may include repeating steps (b) and (c) plural times. The method may also include a step between steps (b) and (c) of supplying a fluid into the reaction chamber to flush away the excess reagent or protecting groups.

As a further optional enhancement the method may include the step of supplying a further solution between the repeating steps (c) and (b). This solution is used to cap or make unreactive any sites on the growing peptide fragments onto which the previous amino acid failed to couple. The capping solution is supplied to the reactor after the amino acid but before the reagent for deprotection. The purpose of the capping is as an aid to later purification of the completed peptide.

The method of the second aspect may include a step of continuously recording the volume of the reaction chamber, and calculating therefrom an indication of an extent of coupling. The method may also calculate an indication of a speed of the coupling from the recorded rate of volume change.

Advantageously, it is possible to estimate the mass change during the continuous flow reaction from the reactor volume change and therefore determine to what extent any particular reaction step has been successful. For example, in a solid phase peptide synthesis reaction, it is possible to determine whether any particular coupling has been successful and to what extent.

The method of second aspect may include the steps of: setting a value for a maximum value of the reaction chamber; and modifying the value for the maximum volume of the reaction chamber based on the stage of the continuous flow reaction. The value of the maximum volume of the reaction chamber may be increased during coupling.

The reaction performed by the second aspect may be performed using a continuous flow reactor as set out in relation to the first aspect or in any of the optional embodiments thereof.

In a third aspect, the invention provides a method of controlling a moveable wall of a reaction chamber of a continuous flow reactor, the method comprising: monitoring a pressure of a fluid within the continuous flow reactor; adjusting the position of the movable wall, to thereby change a reaction volume of the reaction chamber, based on the monitored pressure.

Advantageously, the pressure and/or volume of the reaction chamber during a continuous flow reaction can be controllably adjusted.

The step of monitoring the pressure may include monitoring the pressure at the inlet and monitoring the pressure at the outlet and/or monitoring a differential pressure between the inlet and the outlet or vice-versa. In this way a differential pressure across the reactor can be measured. This can allow for control of the reactor volume and/or for information about the progress of the reaction to be obtained (for example in conjunction with the reactants flowing at known and/or consistent flowrates through the reactor).

In certain arrangements, the step of monitoring the pressure may include monitoring the pressure at the inlet and monitoring the pressure at the outlet.

In further arrangements, the step of monitoring the pressure may include monitoring the pressure at the inlet, whilst the outlet is exposed to atmospheric pressure. In such an arrangement, the outlet pressure is known and therefore the differential pressure between the inlet and outlet can be determined.

In further arrangements, the step of monitoring the pressure may include directly monitoring a differential pressure between the inlet and the outlet.

The position of the moveable wall within the reaction chamber may be adjusted so as to maintain the monitored pressure within a range of 0.1 bar to 15 bar, preferably in a range of 0.5 bar to 15 bar.

The method of the third aspect may include the steps of: defining a set-point for the monitored pressure and a range of pressure changes relative to the set-point over which the volume of the reaction chamber will not be adjusted. The range may be within ±0.05 bar to ±0.5 bar, preferably within ±0.2 bar to ±0.5 bar. The range need not be symmetrical about the set-point.

The method of the third aspect may include adjusting the volume of the reaction chamber with an asymmetric speed, when the monitored fluid pressure changes in one direction, relative to another. The volume of the reaction chamber may be adjusted faster when the monitored fluid pressure increases than when the monitored fluid pressure decreases.

The continuous flow reactor of the third aspect may be the continuous flow reactor as set out in the first aspect or in any optional embodiment thereof.

In a fourth aspect, the invention provides a controller operable to control a continuous flow reactor, the controller being configured to perform the method of either the second or third aspect or any optional embodiments thereof.

The continuous flow reactor of the fourth aspect may be the continuous flow reactor as set out in the first aspect or in any optional embodiment thereof.

When the term 'a fluid pressure in the continuous flow reactor' is used herein, it may be meant that the pressure sensor monitors one or more pressure(s) which are or are indicative of a pressure within the reaction chamber. For example, in an exemplary embodiment, the pressure sensor may be configured to monitor a fluid pressure at the inlet (or in a pipe leading to the inlet) and the same or a different pressure sensor may be configured to monitor a fluid pressure at the outlet (or in a pipe leading to the outlet). In an alternative embodiment, the pressure sensor may measure a differential pressure across the reaction chamber itself or between two points within the continuous flow reactor (which may be, for example, the inlet and the outlet).

Further aspects of the present invention provide: a computer program comprising code which, when run on a computer (for example the controller of the fourth aspect), causes the computer to perform the method of the second or third aspect; and a computer readable medium storing a computer program comprising code which, when run on a computer (such as the controller of the fourth aspect), causes the computer to perform the method of the second or third aspect.

BRIEF DESCRIPTION OF THE DRAWINGS

Embodiments of the invention will now be described by way of example with reference to the accompanying drawings in which.

DETAILED DESCRIPTION AND FURTHER OPTIONAL FEATURES

Embodiments of the present invention are described below. Where optional features are set out, these are applicable singly or in any combination with any aspect of the invention.

Figure 1:
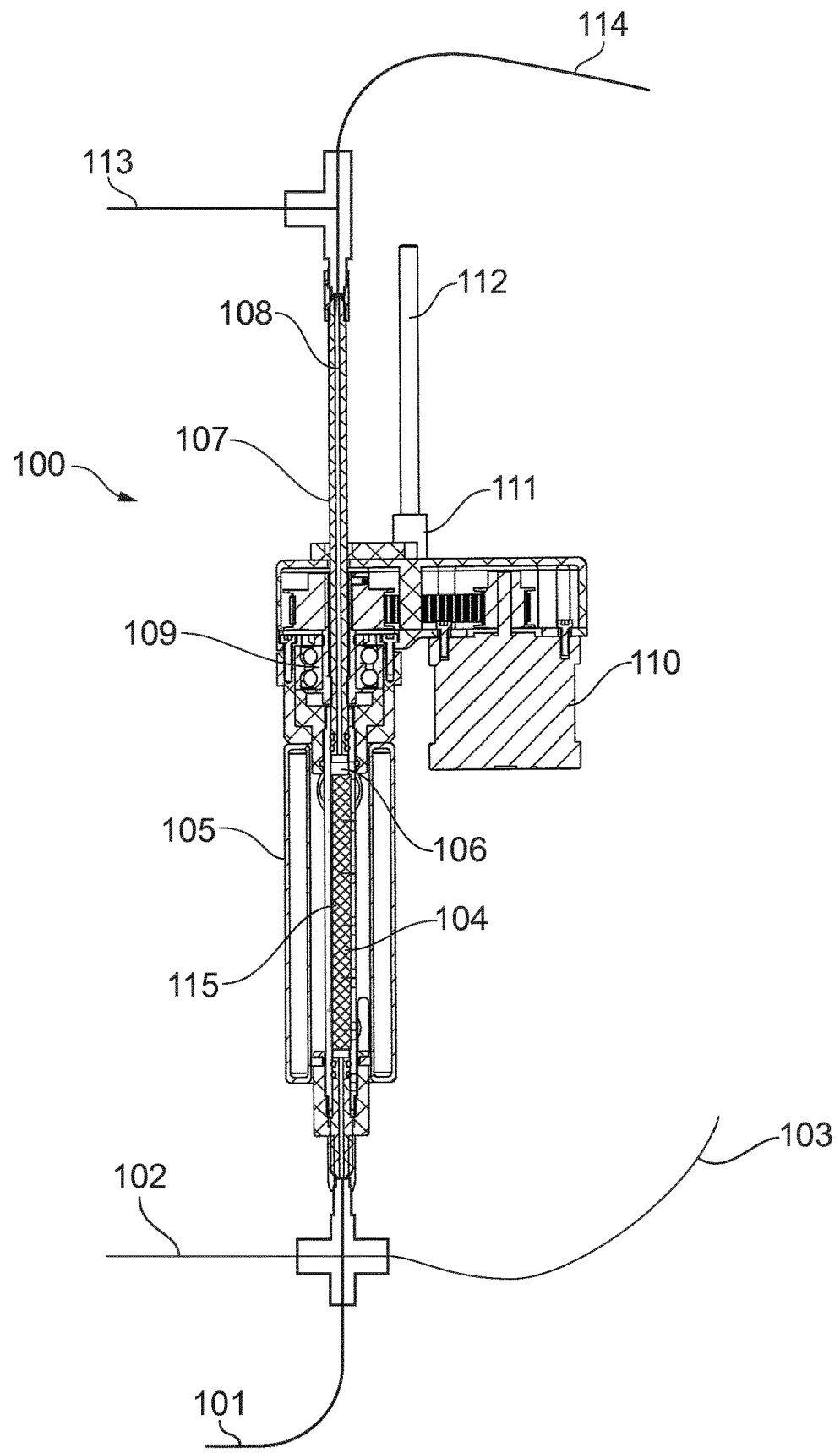
FIG. 1 shows a cross-sectional view of a continuous flow reactor according to the an embodiment of the present invention.

FIG. 1 shows a continuous flow reactor 100 according to a first embodiment of the present invention. The reactor includes a feed stream 101 for a first fluid, for example an activated amino acid, and a feed stream 102 for a second fluid which may be a solution used for deprotection of amino acids. The join between the two feed streams 101 and 102 includes a pressure connector 103 for connecting the join to a pressure sensor (not shown) for measuring a fluid pressure upstream of a reaction chamber 104. Generally the join between the two feed streams is considered the inlet of the reactor.

The reaction chamber is partially defined by a glass column 104 which is contained within a heat exchanger 105. The glass column includes a solid support 115 for use in solid phase peptide synthesis, for example 150 mg of Chlorotrityl chloride resin.

At one end of the reaction chamber is a moveable wall 106 which, in FIG. 1, is a frit connected to the end of a plunger 107. The frit, sometimes called a fritted glass filter, is a ceramic composition used to filter solid particles from a fluid flow. The frit could equally be made of stainless steel or polytetrafluoroethylene. The plunger contains a channel 108 along its length, so that fluid can flow through the frit 106 and to an outlet. The plunger is threaded, so as to engage a correspondingly threaded drive nut or lead screw 109. The threaded drive nut 109 is connected to and driven by a drive motor 110 which thereby alters the volume of the reaction chamber. The drive motor 110 is connected to a pulley (in this example, an AT3 pulley: 18 tooth, 10 mm wide) which transfers rotation of a drive shaft of the motor to the threaded drive nut 109.

The drive motor may be a hybrid stepper motor, or a brushless DC motor with encoder feedback. Attached to the drive motor is an anti-rotation device 111, and a slide rod 112 for the anti-rotation device. The anti-rotation device can function as a mechanical stop for the drive motor 110, to provide a maximum volume and/or minimum volume of the reaction chamber. As an alternative to the anti-rotation device (or in addition thereto) a controller connected to the drive motor may be programmed with maximum and minimum volumes of the reaction chamber, and can act to stop the drive motor exceeding these volumes.

The outlet, provided at the end of the channel 108 in the plunger is connected to a fluid outlet 113 and a pressure connector 114 for connecting to outlet to a pressure sensor (not shown) for measuring a fluid pressure downstream of the reaction chamber 104.

The drive motor 110 is controllable by the controller which may be external or internal to the continuous flow reactor 100, and is connected to the pressure connectors 103 and 114. In response to the pressure sensed from the pressure connectors, the controller can operate the drive motor so as to increase or decrease a reaction volume of the reaction chamber 104 by rotating the lead screw 109 and thereby moving the plunger 107 and frit 106 up or down.

Figure 2:
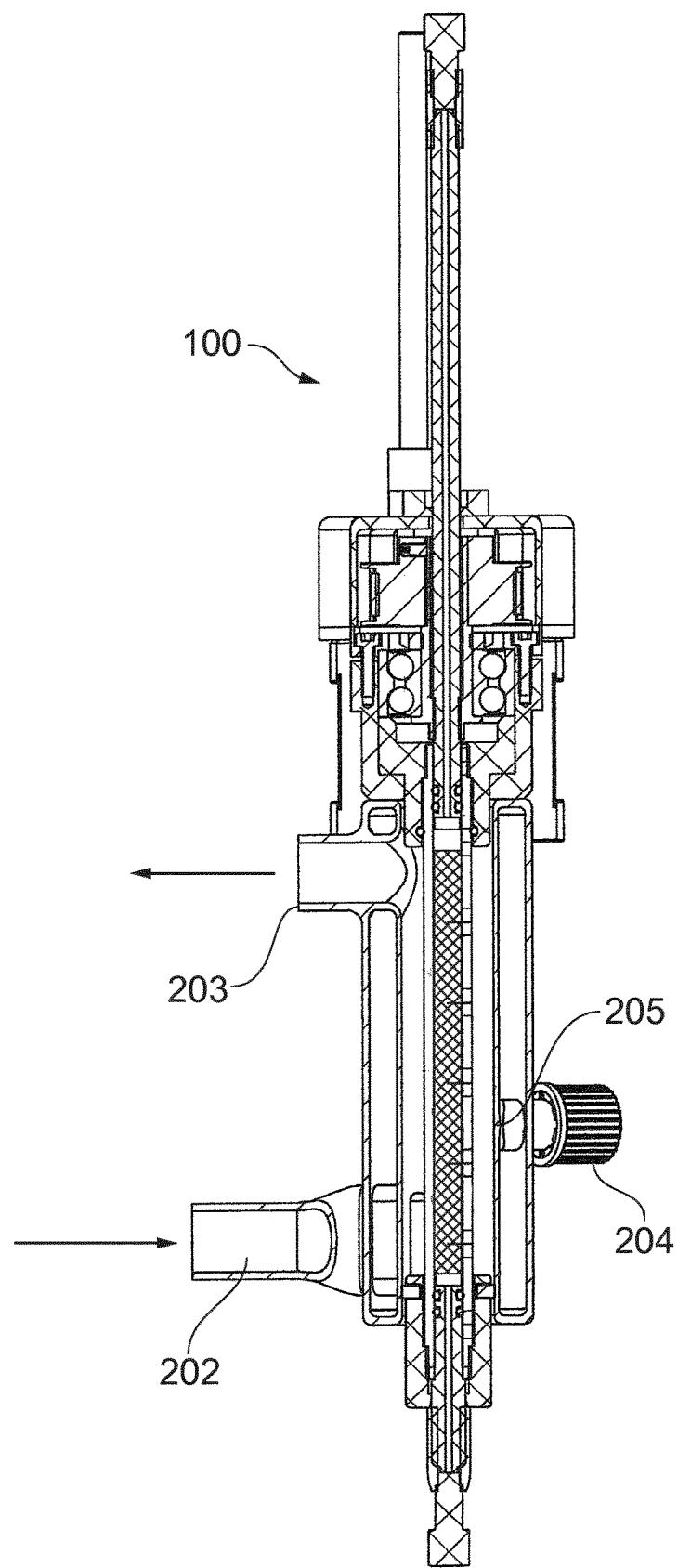
FIG. 2 shows a cross-sectional view of the continuous flow reactor of FIG. 1 rotated by 90°.

FIG. 2 shows the continuous flow reactor 100 shown in FIG. 1 as rotated by 90° about its length (vertical axis). Visible in this view is an inlet 202 and outlet 203 of the heat exchanger 105. The heater exchanger also includes a connector 204 for a temperature sensor 205, for sensing the temperature of fluid provided to the heater exchanger as it passes over the reaction chamber. This sensed temperature can be fed back to the controller.

Figure 3:
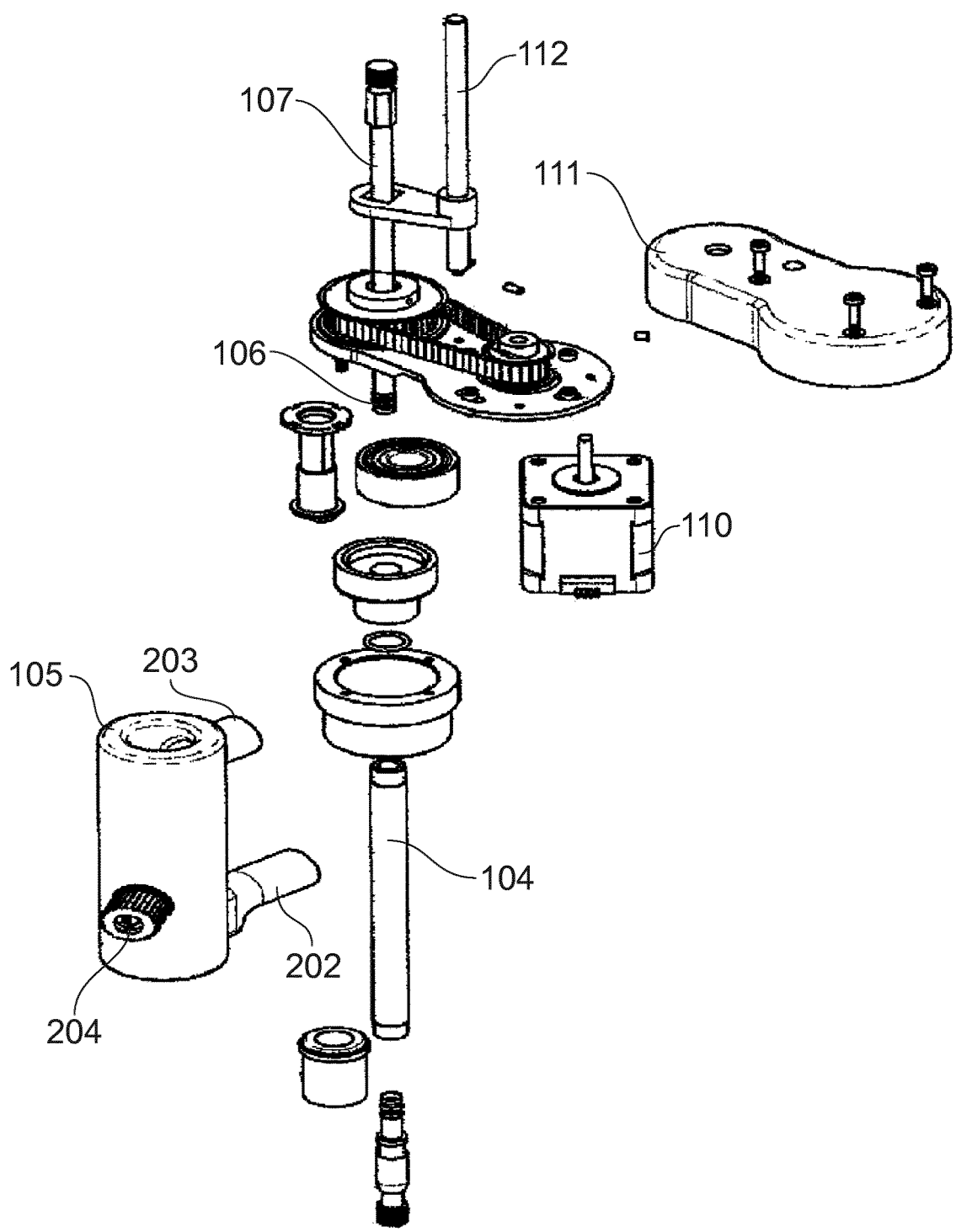
FIG. 3 shows an exploded view of the continuous flow reactor of FIGS. 1 and 2.

FIG. 3 shows an exploded view of the continuous flow reactor 100 discussed above. Like components are indicated by like reference numerals.

Figure 4:
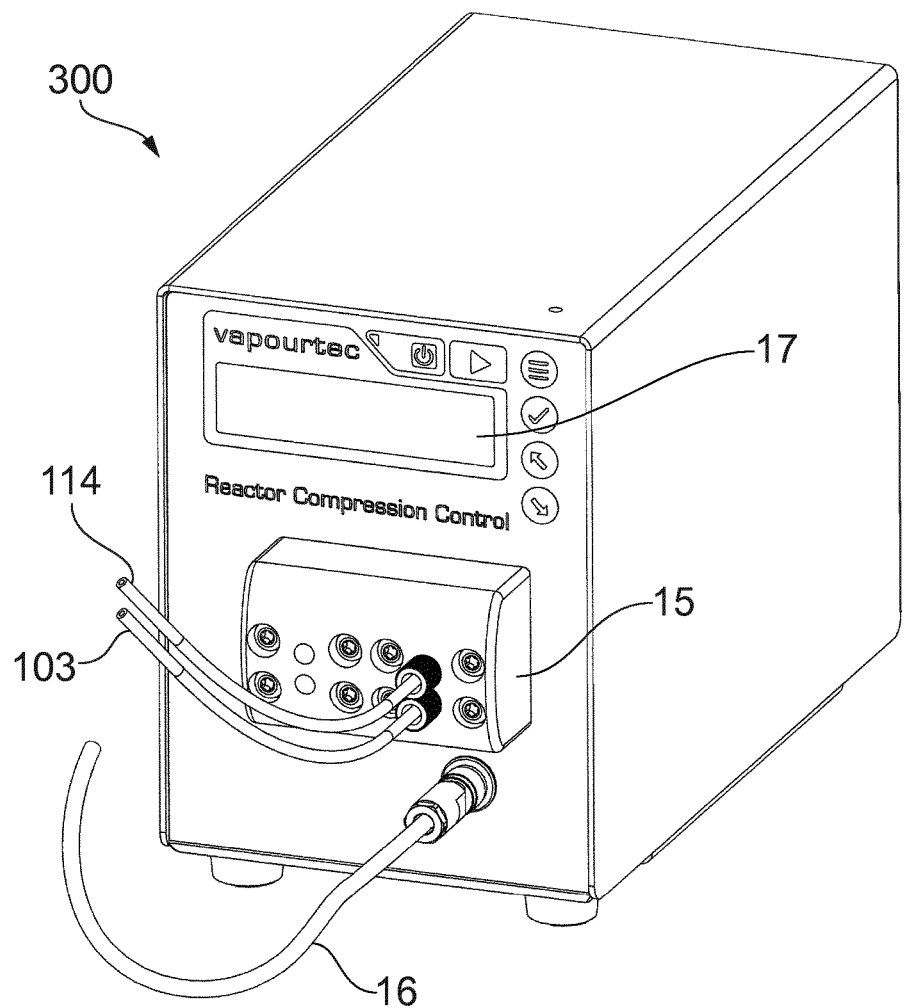
FIG. 4 shows a perspective view of a controller according to an embodiment of the invention.

FIG. 4 illustrates a controller 300 according to a further embodiment of the invention. The controller includes a display 17, and buttons for inputting commands to the controller. A gauge pressure manifold 15 allows connection of pressure connectors 104 and 114, thus the controller can monitor the pressure downstream and upstream of the reaction chamber and is able to calculate a differential pressure between the two. The pressure connectors preferably include ceramic fluid contact surfaces. As an alternative, a single differential pressure sensor can be provided which directly measures a differential pressure between the inlet and outlet of the continuous flow reactor. Also connected to the controller is cable bundle 16 which connects to the drive motor 110.

Figure 5:
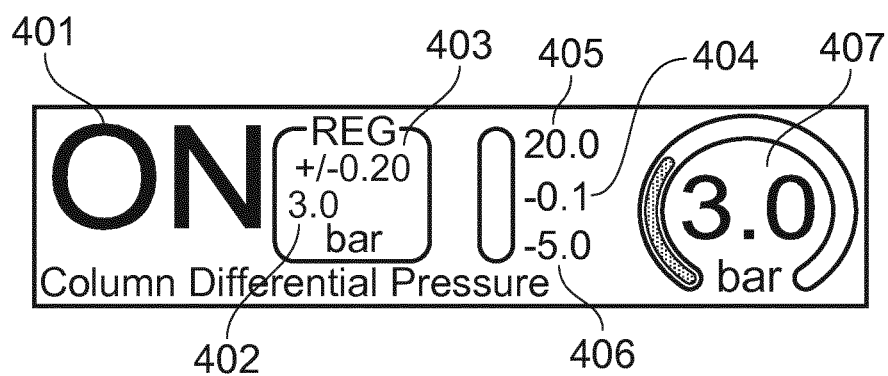
FIG. 5 shows a control interface of the controller of FIG. 4.

FIG. 5 shows an example display 17 of the controller. The display includes a status indicator 401, for informing the user whether the controller is operating or not. A target differential pressure 402 is also displayed, together with a current setting of the dead-band 403 discussed above (i.e. the region of pressure changes over which the controller will not alter the volume of the reaction chamber). The target differential pressure is the differential pressure that the controller is adjusting the volume of the reaction chamber in order to achieve. As discussed above, this is usually set within the range 0.1 bar to 15 bar. The actual current position 404 of the moveable wall is shown (in mm), which is measured relative to a starting position (in this example −0.1 mm from the initial starting position). The maximum allowable plunger position is shown at 405, and the minimum at 406. Again these are measured relative to an initial starting position. The positions may be displayed a resolution of $1/10^{th}$ of a millimetre, but can be controlled to within $1/100^{th}$ of a millimetre. The minimum value may be set so as to prevent the reactor contents from being compressed continually should the current target differential pressure not be achievable (for example in the case where no fluid is flowing or the flowrate is excessively low). The current measured differential pressure is shown at 407.

As discussed above, the maximum allowable plunger position may be modified so as to track with the actual position experience during coupling during peptide synthesis. In this way the reaction chamber can be allowed to expand as the peptide grows but never excessively during a wash cycle at a high flowrate.

In an example of a reaction according to an embodiment of the present invention and using the continuous flow reactor of FIGS. 1-3, residues 65-74 of the acyl carrier protein (ACP, H2N-VQAAIDYING-CONH2, ref: R. B. Merrifield, *J. Am. Chem. Soc.*, 1963, 85 (14), 2149-2154) were synthesised. This peptide is well-known as a challenging sequence due to aggregation phenomena, and is commonly used to evaluate the performance of a synthesis platform. Below the ACP synthesis is used to show how the reactor volume changes during synthesis and then using this example the peptide is synthesised using two different methods to show how the data from the compression controller can be used to predict problematic sequences in any peptide synthesis.

Figure 8:
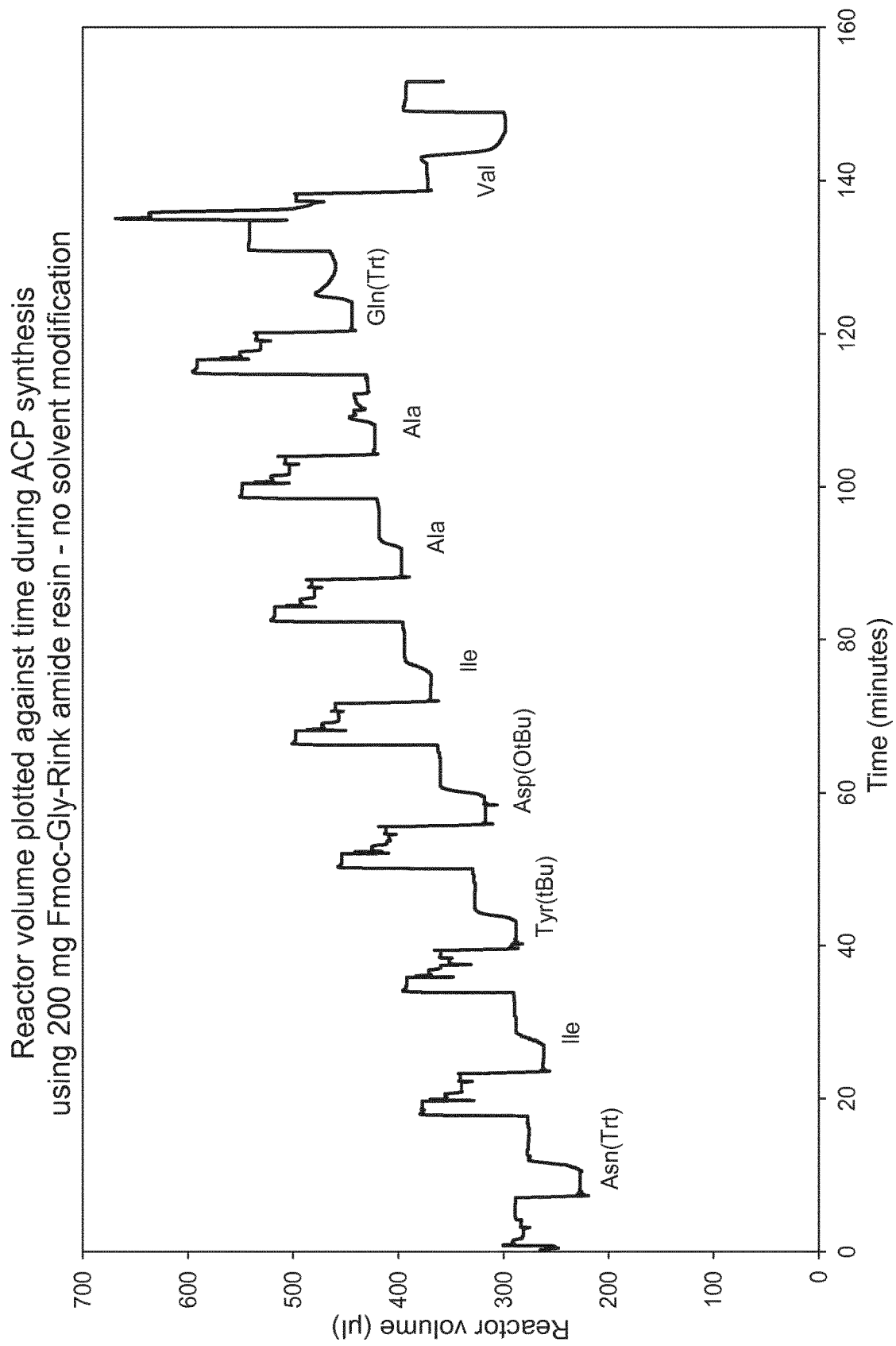
FIG. 8 is a graph showing the reactor volume against time during a further example synthesis.

The 10 mer peptide acyl carrier protein (ACP, H2N-VQAAIDYING-CONH2) is synthesised using a continuous flow reactor of the above embodiments using 400 mg Fmoc-Gly-Rink amide resin. It is assumed that the Fmoc-Gly-Rink amide resin has a loading of 0.8 mmol/g. The fully protected peptide ACP has molecular weight of 1879.96 g/mol. Therefore, assuming no losses, after synthesis and before cleavage the 0.4 g of resin will have a mass of 0.4+(1879.96×0.4×0.8/1000)=1.002 g. It is clear that the reactor must change in volume to accommodate the additional 0.602 g of mass unless the density of the packed bed is to increase markedly. In reality, when this peptide is synthesised the volume of the reactor is observed to increase by a factor of 2.5 (see FIG. 6). For the example shown in FIG. 6 a solvent modification was implemented for the final two couplings to prevent aggregation of the peptide. FIG. 8 shows the same synthesis but without the solvent modification.

Figure 6:
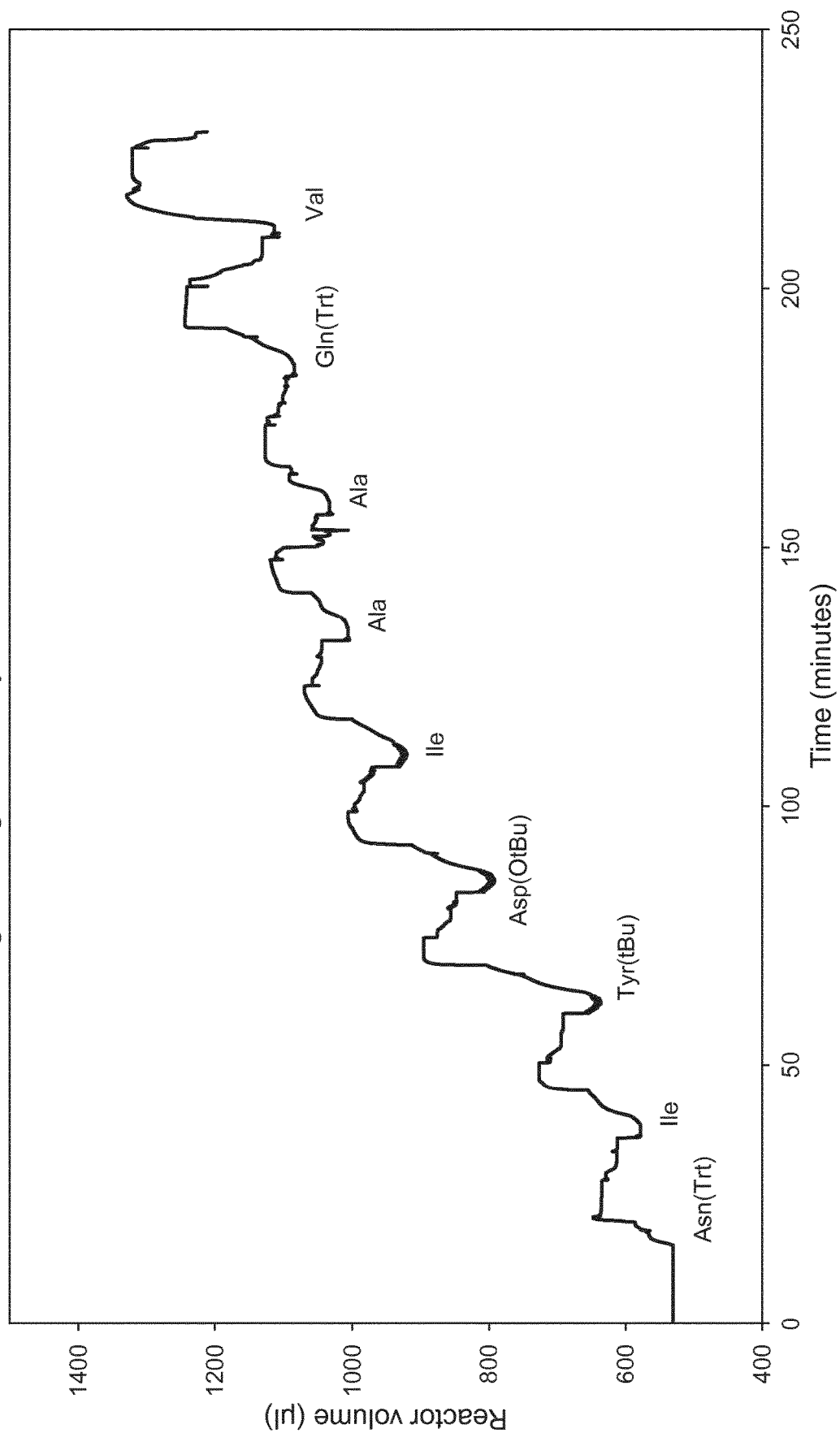
FIG. 6 is a graph showing the reactor volume against time during an example synthesis.

FIG. 6 shows the data derived from the reactor controller when synthesising the 10-mer peptide ACP using 400 mg of Fmoc-Gly-Rink amide resin. The first 7 couplings were completed using 100% dimethylformamide (DMF) as the solvent. The final two couplings were completed using a 1:1 mixture of DMF and dimethyl sulfoxide (DMSO). The change in the solvent was necessary to prevent aggregation of the peptide. The data from the reactor controller shows a continuous growth for the reactor during all 9 couplings and the corresponding HPLC of the crude peptide (FIG. 7) indicates purity of 90%.

Figure 7:
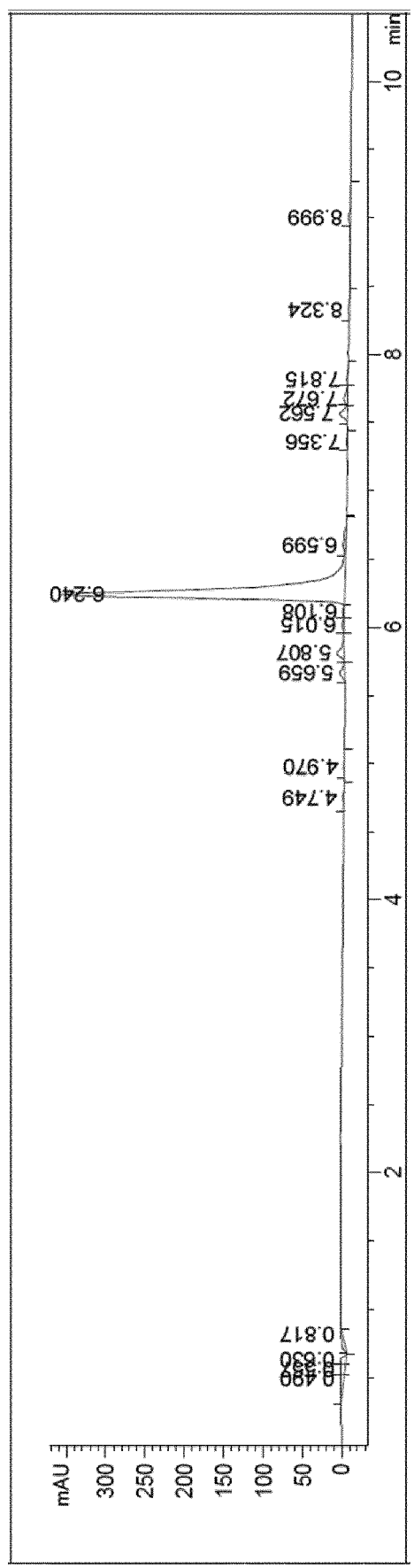
FIG. 7 is an HPLC plot of the peptide resulting from the reaction shown in FIG. 6.
Figure 9:
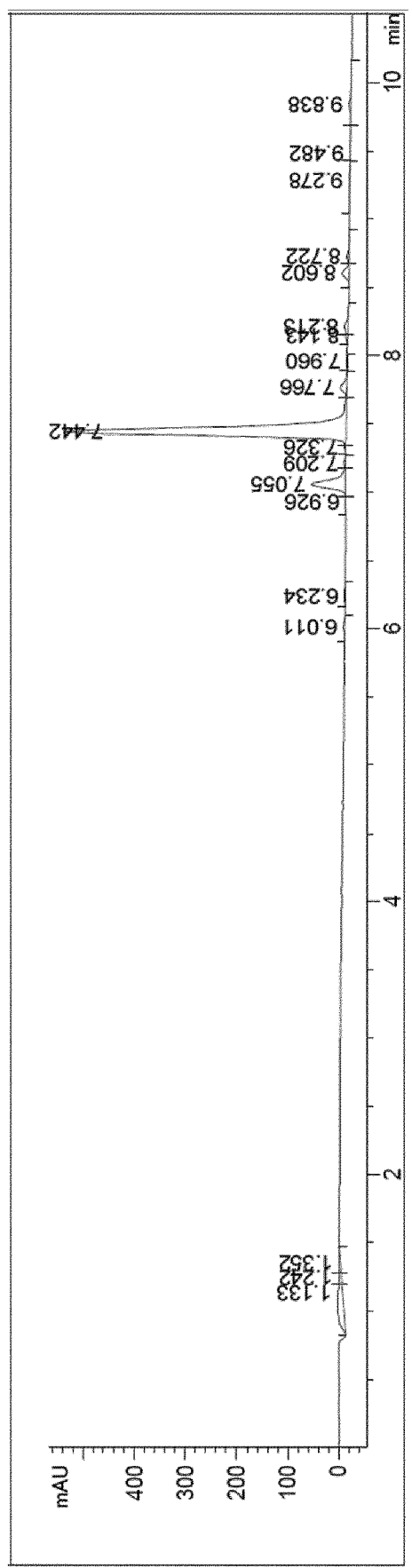
FIG. 9 is an HPLC plot of the peptide resulting from the reaction shown in FIG. 8.

FIG. 7 shows the data derived from the reactor controller when synthesising the 10-mer peptide ACP using 200 mg of Fmoc-Gly-Rink amide resin. All 9 couplings were completed using 100% dimethylformamide (DMF) as the solvent. The data from the reactor controller shows a continuous growth for the reactor during the first 8 couplings but during the final coupling (Valine) at 137 minutes the volume of the reactor is observed to reduce rapidly. This reduction is volume can be attributed to aggregation of the peptide. This type of aggregation is known to hinder the efficiency of coupling. The HPLC trace (FIG. 9) shows a significant peak at 7.055 minutes which is consistent with a proportion of the peptide without the Valine coupled. The crude peptide indicates purity of 80%. The contrast between the data in FIG. 6 and FIG. 8 clearly shows capability of the reactor controller to monitor the coupling and indicate the exact time when a peptide synthesis has become problematic.

Figure 10:
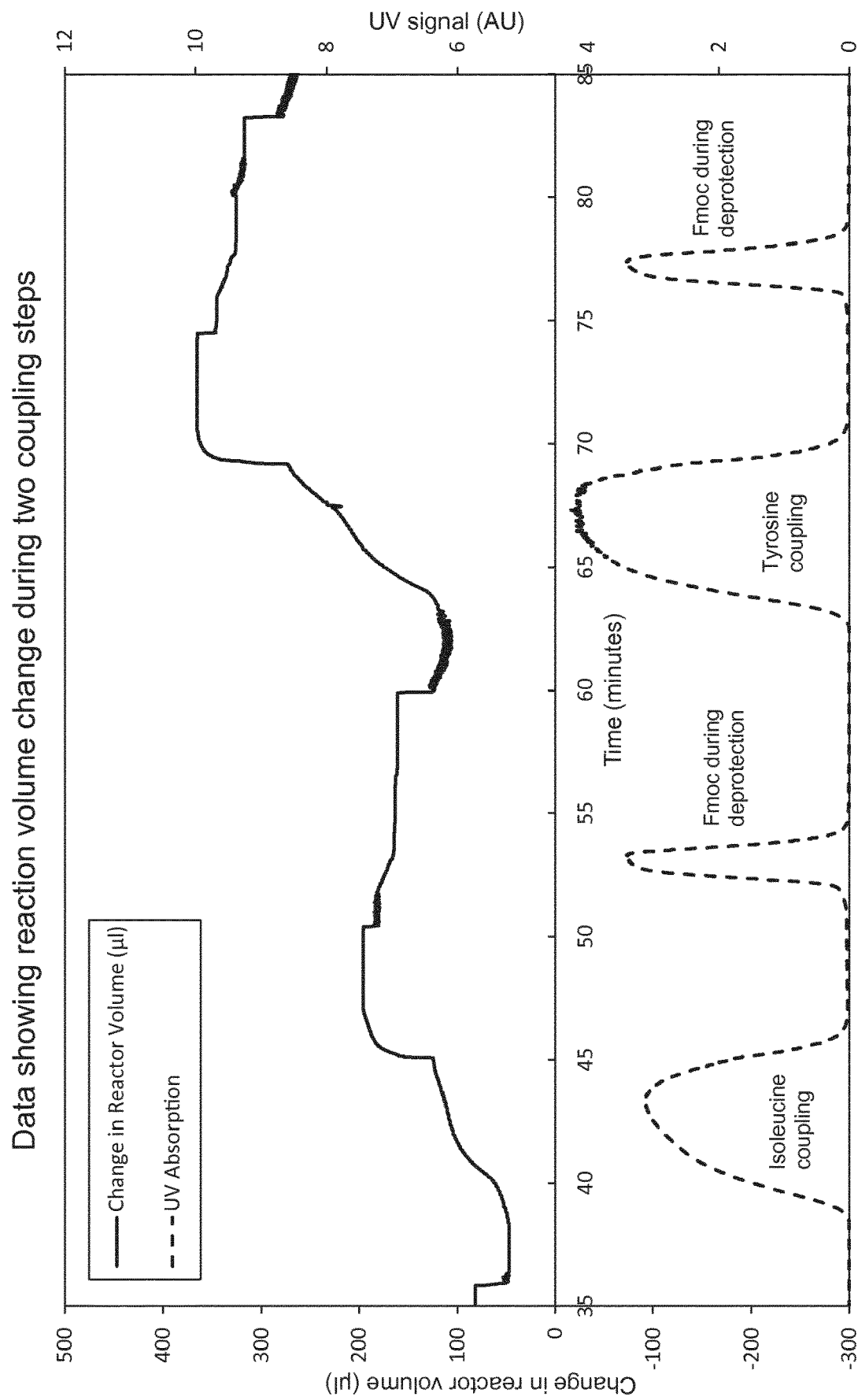
FIG. 10 is a detailed view of the reactor volume for the coupling and deprotection of two amino acids during an example synthesis.

FIG. 10 is a graph showing the reactor volume logged by the controller in the ACP synthesis for the coupling and deprotection of two of the amino acids, Isoleucine and Tyrosine. Also shown is the UV absorption recorded (dotted line) at 312 nm by a UV cell located immediately downstream of the reactor. The flow rates of solvent/reagent through each coupling and deprotection step was identical. The flowrates for Isoleucine coupling and deprotection are detailed as follows:

Time 35.8 min to 45.1 min, coupling at 1.4 ml/min
Time 45.1 min to 50.4 min, post coupling wash at 3 ml/min
Time 50.4 min to 54.4 min, deprotection at 2 ml/min
Time 54.4 min to 59.9 min, post deprotection wash at 2 ml/min The coupling, wash steps and deprotection are at different flowrates which is why the reactor volume changes rapidly immediately after coupling is complete. It is important to note that the two amino acids have very different height/time profiles. At a given flowrate, the profile during coupling is a combination of a number of parameters; molecular weight of the protected amino acid, amount of swelling of the resin by a particular amino acid, rate of coupling, rate of loss of the peptide fragment from the resin (this can occur with some resins and is not desirable). The data obtained during the coupling stage is most valuable in determining the extent and speed of coupling but also in identifying changes in the structure of the peptide.

While the invention has been described in conjunction with the exemplary embodiments described above, many equivalent modifications and variations will be apparent to those skilled in the art when given this disclosure. Accordingly, the exemplary embodiments of the invention set forth above are considered to be illustrative and not limiting. Various changes to the described embodiments may be made without departing from the spirit and scope of the invention.

All references referred to above are hereby incorporated by reference.

LIST OF FEATURES

100 Continuous flow reactor
101, 102 Feed stream
103, 114 Pressure connector
105 Heat exchanger
106 Moveable wall
107 Plunger
108 Channel
109 Lead screw
110 Drive motor
111 Anti-rotation device
112 Slide rod
113 Fluid outlet
115 Solid support
202 Heat exchanger fluid inlet
203 Heat exchanger fluid outlet
204 Temperature connector
205 Temperature sensor
300 Controller
17 Display
15 Pressure manifold
16 Cable bundle
401 Status indicator
402 Target pressure
403 Dead-band setting
404 Current plunger position
405 Maximum plunger position
406 Minimum plunger position
407 Current measured pressure

The invention claimed is:

1. A continuous flow reactor comprising:
an inlet;
an outlet; and
a reaction chamber, between the inlet and the outlet and providing a flow path therebetween, the reaction chamber having a moveable wall;
the reactor further comprising:
a pressure sensor, configured to monitor a differential fluid pressure in the continuous flow reactor between the inlet and the outlet; and
a controller, operable to adjust the position of the moveable wall, and thereby change a volume of the reaction chamber, based on the monitored fluid pressure.

2. The continuous flow reactor of claim 1, wherein the moveable wall is connected to a drive system including a motor and a lead screw.

3. The continuous flow reactor of claim 2, wherein the drive mechanism includes a stop, configured to provide a minimum volume of the reaction chamber and/or a maximum volume of the reaction chamber.

4. The continuous flow reactor of claim 1, wherein the moveable wall includes a frit which at least partially defines a wall of the reaction chamber.

5. The continuous flow reactor of claim 4, wherein the moveable wall includes a fluid pathway disposed therein fluidly connecting the reaction chamber to the outlet.

6. The continuous flow reactor of claim 1, wherein the controller is programmable with a range of pressure changes relative to the set-point over which it will not adjust the position of the sidewall.

7. The continuous flow reactor of claim 1, wherein the reaction chamber includes a solid support for use in a flow reaction.

8. The continuous flow reactor of claim 1, wherein the pressure sensor includes a first pressure sensor arranged to measure a pressure at the inlet and a second pressure sensor arranged to measure a pressure at the outlet.

9. The continuous flow reactor of claim 1, wherein the pressure sensor monitors a differential pressure between the inlet and the outlet.

10. The continuous flow reactor of claim 1, wherein the controller is programmed with an asymmetric sensitivity to the monitored fluid pressure, such that it adjusts the position of the sidewall faster in response to a change in the monitored fluid pressure in one direction to another.

11. The continuous flow reactor of claim 1, wherein the controller is programmable with a value for a maximum volume of the reaction chamber; and is operable to modify the value for the maximum volume of the reaction chamber based on a stage of a continuous flow reaction.

12. A method of performing a continuous flow reaction, comprising:
supplying a fluid, via an inlet, into a reaction chamber;
extracting the fluid from the reaction chamber, via an outlet;
monitoring a differential pressure of the fluid within the continuous flow reactor between the inlet and the outlet; and
adjusting a volume of the reaction chamber, based on the monitored fluid pressure between the inlet and the outlet.

13. The method of claim 12, including the step of:
defining a set-point for the monitored pressure and a range of pressure changes relative to the set-point over which the volume of the reaction chamber will not be adjusted.

14. The method of claim 12, wherein the volume of the reaction chamber is adjusted with an asymmetric speed, such that when the monitored fluid pressure changes in one direction the volume is changed at a different rate to when the monitored fluid pressure changes in another direction.

15. The method of claim 12, comprising the steps of:
(a) supplying an amino acid containing fluid into the reaction chamber, the reaction chamber containing a solid support such that the amino acid attaches to the solid support;
(b) supplying a reagent into the reaction chamber, the reagent acting to deprotect the amino acid; and
(c) supplying a further amino acid containing fluid into the reaction chamber, the further amino acid coupling with the amino acid attached to the solid support.

16. The method of claim 15, including a step of:
continuously recording the volume of the reaction chamber, and calculating therefrom an indication of an extent of coupling.

17. The method of claim 15, including the steps of:
setting a value for a maximum volume of the reaction chamber; and
modifying the value for the maximum volume of the reaction chamber based on the stage of the continuous flow reaction.

18. A method of controlling a moveable wall of a reaction chamber of a continuous flow reactor, the method comprising:
monitoring a differential pressure of a fluid within the continuous flow reactor between the inlet and the outlet;
adjusting the position of the moveable wall, to thereby change a reaction volume of the reaction chamber, based on the monitored pressure.

19. The method of claim 18, including the steps of:
defining a set-point for the monitored pressure and a range of pressure changes relative to the set-point over which the volume of the reaction chamber will not be adjusted.

20. The method of claim 18, wherein the volume of the reaction chamber is adjusted with an asymmetric speed, when the monitored fluid pressure changes in one direction, relative to another.

* * * * *